(12) United States Patent
Ormsby et al.

(10) Patent No.: US 8,308,722 B2
(45) Date of Patent: *Nov. 13, 2012

(54) HOLLOW CONDUCTIVE COAXIAL CABLE FOR RADIO FREQUENCY BASED TISSUE ABLATION SYSTEM

(75) Inventors: Theodore C. Ormsby, Escondido, CA (US); George L. Leung, San Diego, CA (US); Gwo Jenn Shen, Carlsbad, CA (US); Peter Chu, Poway, CA (US); Ming Fan Law, San Diego, CA (US)

(73) Assignee: MedWaves, Inc., San Diego, CA (US)

( * ) Notice: Subject to any disclaimer, the term of this patent is extended or adjusted under 35 U.S.C. 154(b) by 1485 days.

This patent is subject to a terminal disclaimer.

(21) Appl. No.: 11/781,467

(22) Filed: Jul. 23, 2007

(65) Prior Publication Data

US 2008/0015570 A1    Jan. 17, 2008

Related U.S. Application Data

(60) Continuation of application No. 11/551,162, filed on Oct. 19, 2006, now abandoned, which is a continuation-in-part of application No. 11/359,808, filed on Feb. 22, 2006, now Pat. No. 7,815,637, which is a division of application No. 10/306,757, filed on Nov. 27, 2002, now Pat. No. 7,004,938, application No. 11/781,467, which is a continuation of application No. 11/479,259, filed on Jun. 30, 2006, now Pat. No. 7,594,913, which is a continuation-in-part of application No. 10/637,325, filed on Aug. 8, 2003, now Pat. No. 7,070,595, which is a continuation-in-part of application No. 10/306,757, filed on Nov. 27, 2002, now Pat. No. 7,004,938, said application No. 10/637,325 is a continuation-in-part of application No. 09/459,058, filed on Dec. 11, 1999, now Pat. No. 6,663,625, which is a continuation-in-part of application No. 09/211,188, filed on Dec. 14, 1998, now Pat. No. 6,190,382.

(60) Provisional application No. 60/334,199, filed on Nov. 29, 2001.

(51) Int. Cl.
*A61B 18/18* (2006.01)
(52) U.S. Cl. ............. 606/41; 606/33; 607/101; 607/156
(58) Field of Classification Search ............. 606/32–33, 606/39
See application file for complete search history.

(56) References Cited

U.S. PATENT DOCUMENTS 2,847,990 A    8/1958   Ayre
(Continued)

FOREIGN PATENT DOCUMENTS

EP    1055399    11/2000
(Continued)

OTHER PUBLICATIONS

International Preliminary Examination Report for PCT/US02/373886, August 21, 2003, 3 pages.
(Continued)

*Primary Examiner* — Linda Dvorak
*Assistant Examiner* — Jaymi Della
(74) *Attorney, Agent, or Firm* — Procopio, Cory, Hargreaves & Savitch LLP

(57) ABSTRACT

A hollow coaxial cable adapted for conduction of radio frequency (RF) energy, particularly microwave energy, has a proximal end and a distal end and comprises coaxial inner and outer conductors extending substantially the entire length of the cable from the proximal end to a distal end portion of the cable with a dielectric medium disposed between the inner and outer conductors. The inner conductor comprises an elongated electrically conductive tubular member having a hollow, axially extending lumen, and the outer conductor comprises an elongated electrically conductive tubular member disposed in a substantially coaxial relationship over at least a portion of the inner conductor. An ablating member which delivers radio frequency energy, particularly microwave energy, to body tissue is disposed at a distal end portion of the cable.

19 Claims, 8 Drawing Sheets

U.S. PATENT DOCUMENTS

| | | | |
|---|---|---|---|
| 3,058,473 A | | 10/1962 | Whitehead |
| 3,309,455 A | | 3/1967 | Mildner |
| 3,521,620 A | | 7/1970 | Cook |
| 3,552,384 A | | 1/1971 | Pierie et al. |
| 4,204,549 A | * | 5/1980 | Paglione ............... 607/102 |
| 4,271,848 A | * | 6/1981 | Turner et al. ............ 607/101 |
| 4,408,089 A | | 10/1983 | Nixon |
| 4,583,556 A | | 4/1986 | Hines et al. |
| 4,723,936 A | | 2/1988 | Buchbinder et al. |
| 4,776,086 A | | 10/1988 | Kasevich |
| 4,906,230 A | | 3/1990 | Maloney et al. |
| 4,960,134 A | | 10/1990 | Webster, Jr. |
| 5,150,717 A | | 9/1992 | Rosen et al. |
| 5,275,597 A | * | 1/1994 | Higgins et al. ............ 606/33 |
| 5,298,682 A | | 3/1994 | Salz |
| 5,346,392 A | * | 9/1994 | Kim ....................... 431/277 |
| 5,366,490 A | * | 11/1994 | Edwards et al. ........... 607/99 |
| 5,370,644 A | | 12/1994 | Langberg |
| 5,370,677 A | * | 12/1994 | Rudie et al. ............ 607/101 |
| 5,462,545 A | | 10/1995 | Wang et al. |
| 5,476,495 A | | 12/1995 | Kordis et al. |
| 5,496,271 A | | 3/1996 | Burton et al. |
| 5,500,012 A | | 3/1996 | Brucker et al. |
| 5,545,193 A | | 8/1996 | Fleischman et al. |
| 5,617,854 A | | 4/1997 | Munsif |
| 5,642,736 A | | 7/1997 | Avitall |
| 5,656,029 A | | 8/1997 | Imran et al. |
| 5,656,796 A | | 8/1997 | Marinos et al. |
| 5,683,382 A | | 11/1997 | Lenihan et al. |
| 5,697,958 A | * | 12/1997 | Paul et al. ............... 607/31 |
| 5,702,433 A | | 12/1997 | Taylor et al. |
| 5,738,683 A | | 4/1998 | Osypka |
| 5,741,249 A | | 4/1998 | Moss et al. |
| 5,752,951 A | | 5/1998 | Yanik |
| 5,755,754 A | | 5/1998 | Rudie et al. |
| 5,776,176 A | | 7/1998 | Rudie |
| 5,785,706 A | | 7/1998 | Bednarek |
| 5,788,692 A | | 8/1998 | Campbell et al. |
| 5,800,482 A | | 9/1998 | Pomeranz et al. |
| 5,800,494 A | | 9/1998 | Campbell et al. |
| 5,810,717 A | | 9/1998 | Maeda et al. |
| 5,837,001 A | | 11/1998 | Mackey |
| 5,842,984 A | | 12/1998 | Avitall |
| 5,843,076 A | | 12/1998 | Webster, Jr. et al. |
| 5,849,028 A | | 12/1998 | Chen et al. |
| 5,857,997 A | | 1/1999 | Cimino et al. |
| 5,863,291 A | | 1/1999 | Schaer |
| 5,876,373 A | | 3/1999 | Giba et al. |
| 5,882,333 A | | 3/1999 | Schaer et al. |
| 5,885,278 A | | 3/1999 | Fleischman |
| 5,893,885 A | | 4/1999 | Webster, Jr. |
| 5,897,529 A | | 4/1999 | Ponzi |
| 5,902,251 A | | 5/1999 | vanHooydonk |
| 5,904,667 A | | 5/1999 | Falwell |
| 5,916,241 A | | 6/1999 | Rudie et al. |
| 595,796 A | | 9/1999 | Warner et al. |
| 5,971,983 A | | 10/1999 | Lesh |
| 6,014,579 A | | 1/2000 | Pomeranz et al. |
| 6,032,077 A | | 2/2000 | Pomeranz |
| 6,033,403 A | | 3/2000 | Tu et al. |
| 6,067,475 A | | 5/2000 | Graves et al. |
| 6,071,280 A | | 6/2000 | Edwards et al. |
| 6,123,718 A | | 9/2000 | Tu et al. |
| 6,175,768 B1 | * | 1/2001 | Arndt et al. ............ 607/101 |
| 6,183,463 B1 | | 2/2001 | Webster, Jr. |
| 6,190,382 B1 | | 2/2001 | Ormsby |
| 6,230,060 B1 | * | 5/2001 | Mawhinney ............ 607/101 |
| 6,254,568 B1 | | 7/2001 | Ponzi |
| 6,267,746 B1 | | 7/2001 | Bumbalough |
| 6,319,250 B1 | | 11/2001 | Falwell et al. |
| 6,356,790 B1 | | 3/2002 | Maguire et al. |
| 6,383,182 B1 | | 5/2002 | Berube et al. |
| 6,500,167 B1 | | 12/2002 | Webster, Jr. |
| 6,527,769 B2 | | 3/2003 | Langberg |
| 6,592,581 B2 | | 7/2003 | Bowe |
| 6,610,046 B1 | | 8/2003 | Usami et al. |
| 6,610,058 B2 | | 8/2003 | Flores |
| 6,663,622 B1 | | 12/2003 | Foley et al. |
| 6,663,625 B1 | | 12/2003 | Ormsby et al. |
| 6,669,692 B1 | | 12/2003 | Nelson et al. |
| 6,673,068 B1 | | 1/2004 | Berube |
| 6,786,984 B1 | | 9/2004 | Hanada et al. |
| 6,878,147 B2 | | 4/2005 | Prakash et al. |
| 6,893,155 B2 | | 5/2005 | Kaiser et al. |
| 6,907,298 B2 | | 6/2005 | Smits et al. |
| 6,941,953 B2 | | 9/2005 | Feld et al. |
| 7,004,938 B2 | | 2/2006 | Ormsby et al. |
| 7,033,352 B1 | | 4/2006 | Gauthier et al. |
| 7,070,595 B2 | | 7/2006 | Ormsby et al. |
| 7,194,297 B2 | | 3/2007 | Talpade et al. |
| 7,259,640 B2 | | 8/2007 | Brown et al. |
| 7,301,131 B2 | | 11/2007 | Gauthier et al. |
| 7,331,959 B2 | | 2/2008 | Cao et al. |
| 7,346,399 B2 | | 3/2008 | Berube |
| 7,364,566 B2 | | 4/2008 | Elkins et al. |
| 7,387,126 B2 | | 6/2008 | Cox et al. |
| 7,594,913 B2 | | 9/2009 | Ormsby et al. |
| 2001/0007940 A1 | | 7/2001 | Tu et al. |
| 2001/0018596 A1 | | 8/2001 | Selmon et al. |
| 2001/0049491 A1 | | 12/2001 | Shimada |
| 2002/0087151 A1 | | 7/2002 | Mody et al. |
| 2003/0100894 A1 | * | 5/2003 | Mahon et al. .............. 606/41 |
| 2005/0059965 A1 | | 3/2005 | Eberl et al. |
| 2006/0142752 A1 | | 6/2006 | Ormsby et al. |
| 2007/0066972 A1 | | 3/2007 | Ormsby et al. |
| 2009/0082762 A1 | | 3/2009 | Ormsby et al. |

FOREIGN PATENT DOCUMENTS

| | | |
|---|---|---|
| EP | 1151726 | 11/2001 |
| EP | 1151728 A | 11/2001 |
| WO | WO 97/26544 | 7/1997 |
| WO | 00/35363 | 6/2000 |
| WO | WO 00/35363 | 6/2000 |
| WO | WO 02/26146 | 4/2002 |

OTHER PUBLICATIONS

Supplementary European Search Report tor EP99965180 dated Oct. 1, 2001, 2 pages.

International Preliminary Report on Patentability and Written Opinion for PCT/US2007/080819 issued Apr. 22, 2009, 6 pages Supplementary European Search Report for EP02804448.5 dated Oct. 18, 2005, 3 pages.

Communication issued in EP04779679.2, Dec. 12, 2008, 5 pages.

Office Action dated from U.S. Appl. No. 11/781,467 dated Jun. 23, 2011.

Communication of May 16, 2011 and extended European Search Report dated May 4, 2011 for EP 07853876.6.

International Search Report for PCT/US02/37886, Apr. 4, 2003, 3 pages.

International Preliminary Examination Report for PCT/US02/37886, Aug. 21, 2003, 3 pages.

Supplementary European Search Report for EP99965180 dated Oct. 1, 2001, 2 pages.

International Preliminary Report on Patentability and Written Opinion for PCT/US2007/80819, issued Apr. 22, 2009, 6 pages.

Supplementary European Search Report for EP 02804448.5 dated Oct. 19, 2005, 3 pages.

Office Action from CN02826148.8 with translation, dated Dec. 9, 2005, 8 pages.

Office Action from CN200780024951.0 with translation, issued Apr. 28, 2010, 18 pages.

Office Action from CN200480022784.2 with translation, issued Jun. 5, 2009, 13 pages.

Communication issued in EP04779679.2, dated Dec. 12, 2008, 5 pages.

* cited by examiner

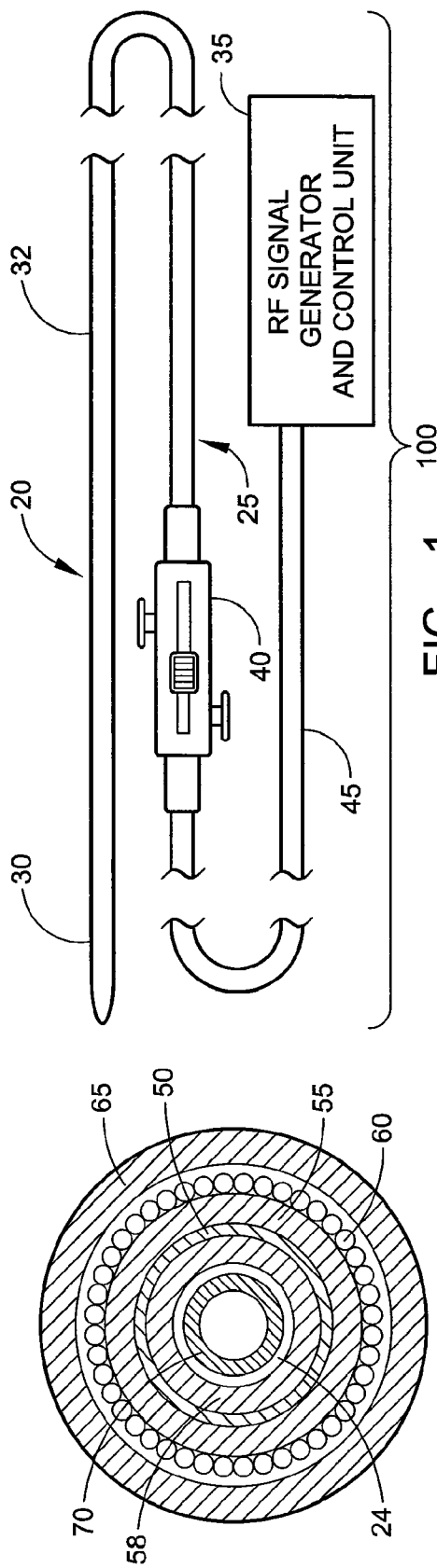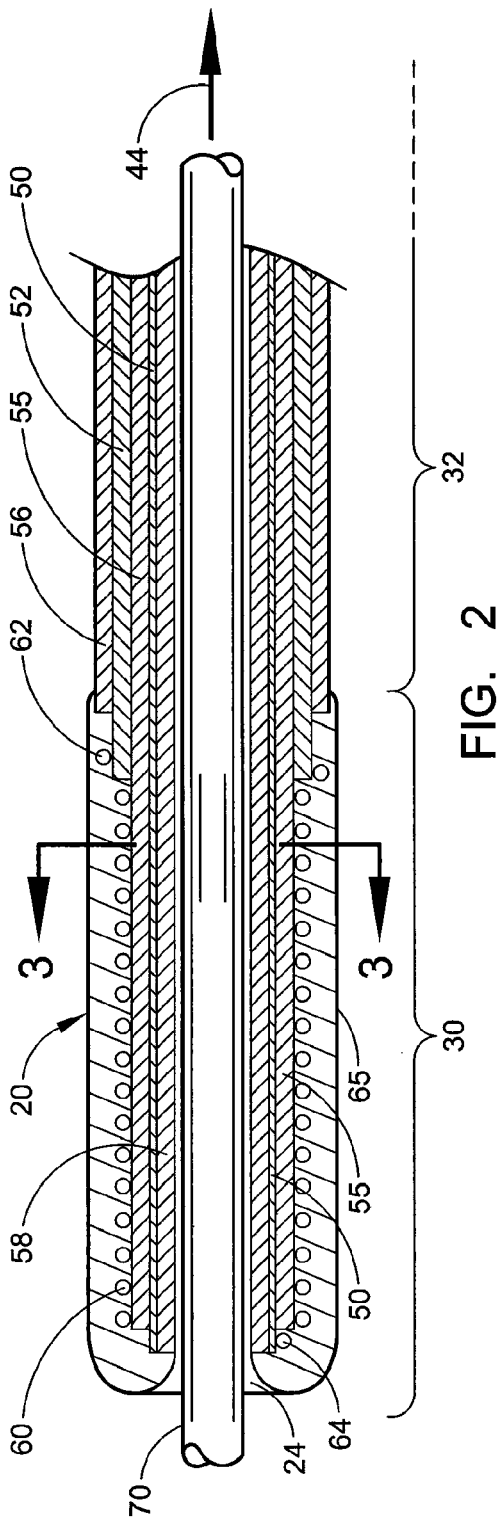

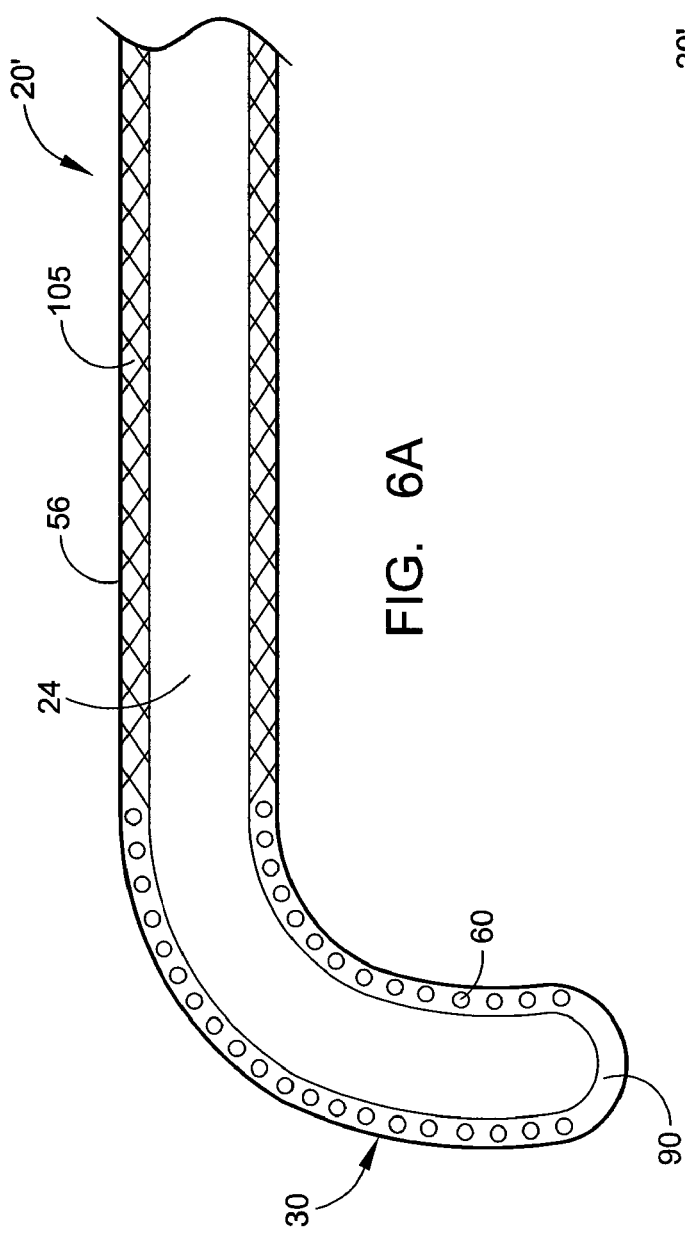
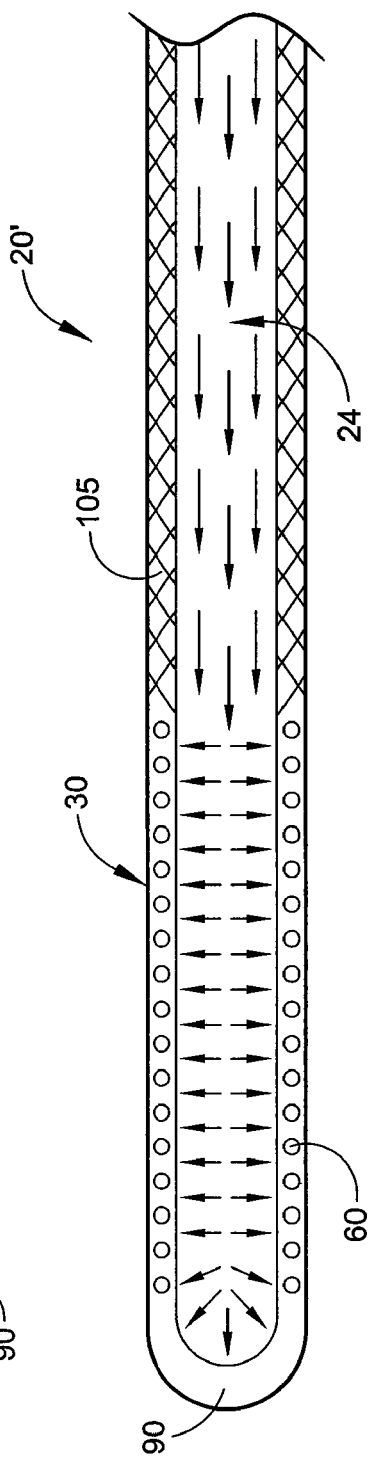

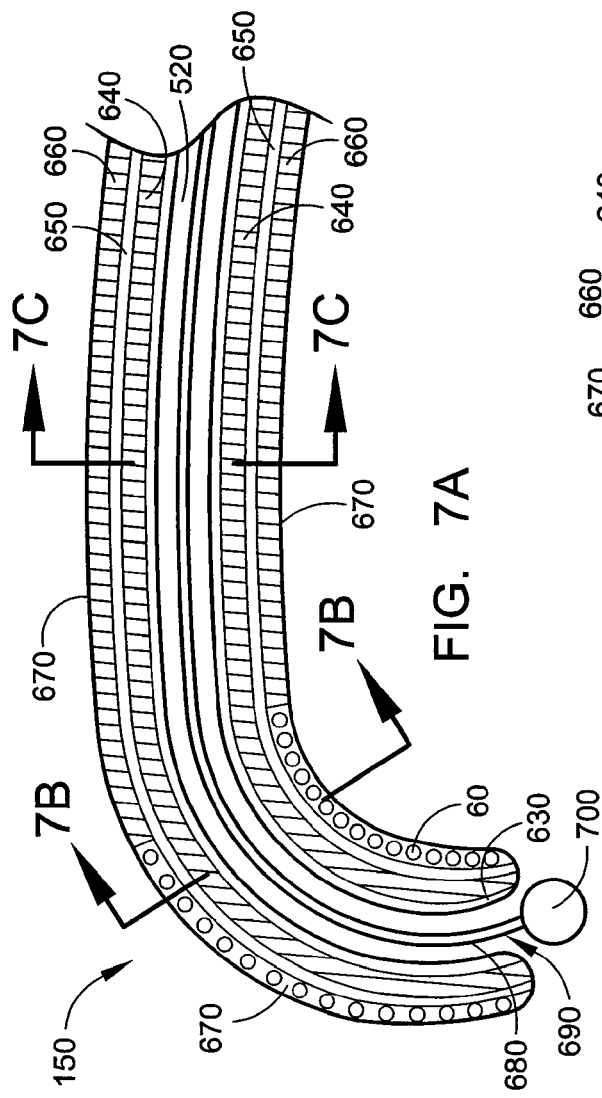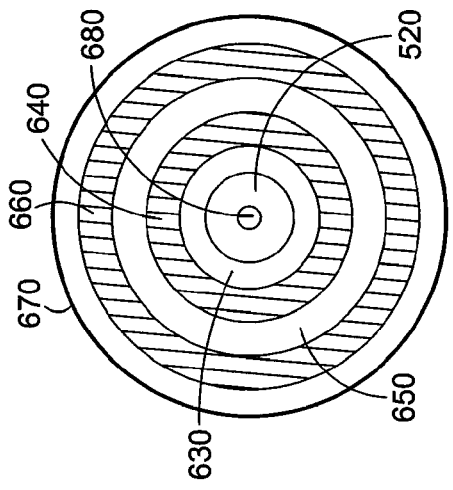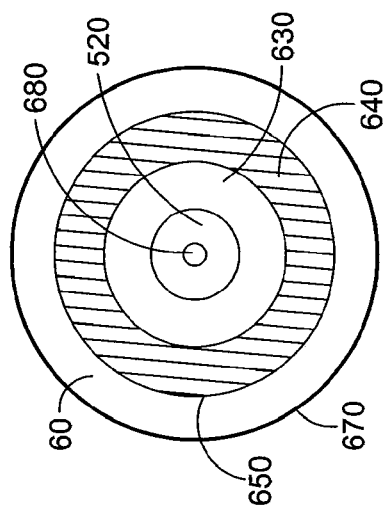

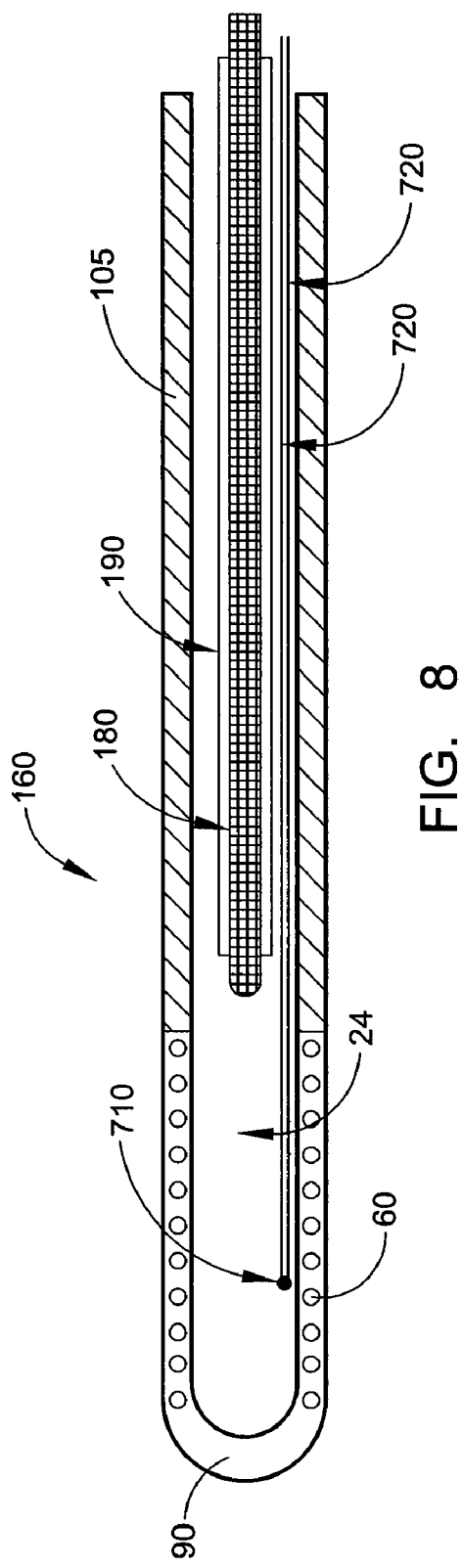
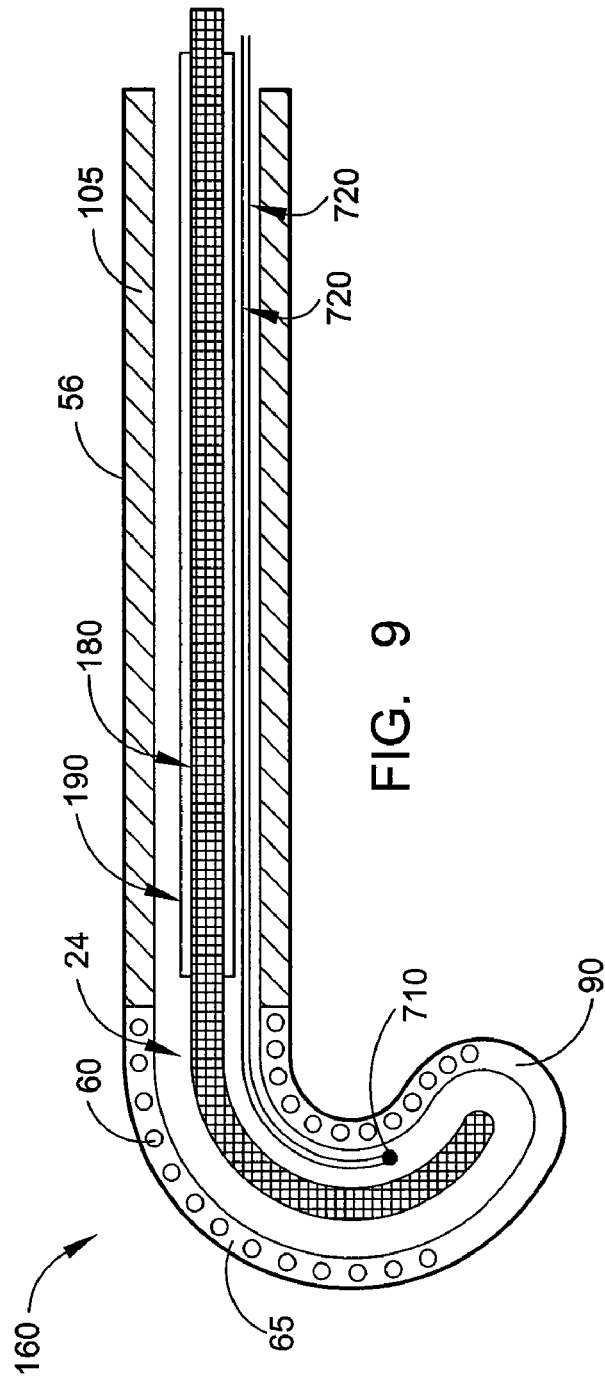

HOLLOW CONDUCTIVE COAXIAL CABLE FOR RADIO FREQUENCY BASED TISSUE ABLATION SYSTEM

RELATED APPLICATIONS

The present application is a continuation of U.S. patent application Ser. No. 11/551,162 of concurrent ownership, filed Oct. 19, 2006 (now abandoned), which is a continuation-in-part of U.S. patent application Ser. No. 11/359,808, filed on Feb. 22, 2006, now U.S. Pat. No. 7,815,637, which is a divisional of U.S. patent application Ser. No. 10/306,757, filed Nov. 27, 2002, now U.S. Pat. No. 7,004,938, which claims the benefit of Provisional Application No. 60/334,199, filed Nov. 29, 2001, and is also a continuation of U.S. patent application Ser. No. 11/479,259 of concurrent ownership, filed on Jun. 30, 2006, now U.S. Pat. No. 7,594,913, which is a Continuation-In-Part of U.S. patent application Ser. No. 10/637,325, filed Aug. 8, 2003, now U.S. Pat. No. 7,070,595, which is a continuation-in-part of U.S. patent application Ser. No. 10/306,757, filed Nov. 27, 2002, now U.S. Pat. No. 7,004,938, which claims the benefit of Provisional Application No. 60/334,199, and which is also a continuation-in-part of U.S. patent application Ser. No. 09/459,058, filed Dec. 11, 1999, now U.S. Pat. No. 6,663,625, which is continuation-in-part of U.S. patent application Ser. No. 09/211,188 filed Dec. 14, 1998, now U.S. Pat. No. 6,190,382. The contents of each of the above identified applications are incorporated herein by reference in their entirety.

BACKGROUND

1. Field of the Invention

The present invention generally relates to medical devices used for irradiation of biological tissues in order to change a property of the biological tissues, such as devices for ablation of biological tissues, and more particularly to a coaxial cable assembly for such devices.

2. Related Art

Tissue ablation systems apply energy to a biological tissue site which requires ablation. Such systems may use various energy modes, such as radiofrequency, ultrasound, laser, cryogenic, and the like. Within the radio frequency (RF) range, certain microwave ablation systems are used to destroy or ablate biological tissues for therapeutic purposes. In one application, microwave ablation systems are used to ablate cardiac tissues that cause irregular heartbeats or arrhythmia, avoiding the need for more risky and invasive open heart surgery. In a microwave ablation procedure, an antenna on a catheter is passed through the vein for access to the atrium. Within the atrium, the antenna is positioned at the desired location where ablation is required. An intracardiac electrogram is used to identify conductive pathways at the cardiac tissue site that needs to be ablated.

Microwave ablation systems are also used in treatment of other areas such as other organs arteries and vessels. In one example, a microwave ablation system is used to ablate tumors in the lungs, liver, kidney or other areas of the body.

Accordingly, what is needed is an efficient system and method for conducting radio frequency energy to an ablating member for delivery of the radio frequency energy to an adjacent tissue site.

SUMMARY

Embodiments described herein provide a new conductive coaxial cable device with a hollow central lumen for use in a radio frequency based tissue ablation system.

In one embodiment, a hollow conductive coaxial cable is provided which comprises a first inner elongated electrically conductive tubular member having a distal end portion, the first tubular member having a hollow, axially extending lumen, a second elongated electrically conductive member disposed in a substantially coaxial relationship over at least a portion of the first electrically conductive tubular member over substantially the length of the cable, a dielectric medium disposed between the first and second electrically conductive tubular members, and an ablating member which delivers radio frequency energy including microwaves to body tissue disposed at the distal end portion of the cable.

In one embodiment, the distal end portion of the cable is selectively or optionally bendable or provided with deflection capability to accommodate the contour of a body vessel or cavity adjacent a biological tissue site to be treated. In one embodiment, a control or guide member for controlling the bending of the distal end portion of the cable extends through the hollow lumen of the inner tubular member in order to control the contour of the distal end portion. The control or guide member is used to shape the distal end portion of the cable as needed during movement to a treatment site.

In one embodiment, the ablating member comprises a radio-frequency transmitter or antenna, which may be a helical coil having one end connected to the inner conductive member and a second end connected to the outer conductive member. A radio frequency signal generator is connected to the proximal end of the cable to generate a train of RF pulses along the cable to the RF antenna, along with a controller or control unit for adjusting the RF signal according to predetermined parameters. In one embodiment, the radio frequency may be a microwave frequency from approximately 300 MHz and up.

In one embodiment, a sensor detects a reflected signal and a forward signal of the RF energy pulses by the RF signal generator, and a controller connected to the sensor determines a voltage standing wave ratio (VSWR) based on the reflected and forward signal. The output frequency of the RF signal may be adjusted based on the VSWR to effect a substantial match of a coaxial cable impedance with RF antenna and biological tissue load impedance. One or more electrodes may be disposed at the distal end portion of the cable. In one embodiment, the electrode or electrodes are of conductive polymer material with hydrophilic characteristics for improved wetability. Two spaced electrode rings are mounted on or embedded in an outer, non-conductive surface layer of the cable. Alternatively, one electrode ring may be provided and the other electrode may be a tip of conductive polymer material at the distal end of the cable. In alternative embodiments, layers of conductive and nonconductive polymer material may be provided at specific positions at the distal end portion of the catheter to produce multiple working electrodes. In each case, the electrode output signal can be connected to a suitable electrode recording system input in the control unit or a separate electrocardiogram unit to provide intracardiac signal mapping.

In one embodiment, a temperature sensor is integrated with the cable and linked to the control unit which monitors temperature at a tissue ablation site. The temperature sensor may be located at or adjacent the distal end of the cable and connected to conductive wires or connectors which extend through the hollow lumen of the inner conductive tubular member to the proximal end of the cable. In one embodiment, the temperature sensor is also located in the hollow lumen at or adjacent the distal end of the cable.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is a schematic block diagram, partially broken away, illustrating one embodiment of radio-frequency ablation system using a conductive cable;

FIG. 2 is a longitudinal cross-sectional view through the distal end portion of a first embodiment of a hollow conductive coaxial cable for the ablation system of FIG. 1;

FIG. 3 is a cross-section on the lines 3-3 of FIG. 2;

FIGS. 6A and 6B are sectional views of the distal end portion of another embodiment of the coaxial cable;

FIG. 7A is a partial side sectional view of the distal end portion of another embodiment of a coaxial cable;

FIG. 7B is a cross-sectional view taken along lines 7B-7B of FIG. 7A;

FIG. 7C is a cross-sectional view taken along lines 7C-7C of FIG. 7A;

FIG. 8 is a cross-sectional view of the distal end portion of a modified coaxial cable incorporating a temperature sensor according to another embodiment of the invention;

FIG. 9 is a cross-sectional view similar to FIG. 8 illustrating the distal end portion of the cable of FIG. 10 in a different configuration;

DETAILED DESCRIPTION

Certain embodiments as disclosed herein provide for a hollow conductive coaxial cable which connects an RF signal generator connected to a proximal end of the cable to an ablation member at a distal end portion of the cable for ablation of biological tissues in body areas such as the heart, liver, and the like.

After reading this description, it will become apparent to one skilled in the art how to implement the invention in various alternative embodiments and alternative applications. However, although various embodiments of the present invention will be described herein, it is understood that these embodiments are presented by way of example only and not limitation. As such, this detailed description of various alternative embodiments should not be construed to limit the scope or breadth of the present invention as set forth in the appended claims.

FIG. 1 illustrates a radio-frequency ("RF") ablation system 100 including an elongate coaxial cable device 20 adapted for placement adjacent a biological tissue site of a patient and incorporating an ablation device such as an RF antenna for delivering electromagnetic energy to a treatment site, as described in more detail below. The cable may be placed adjacent to or within biological tissues or vessels.

Figure 12:
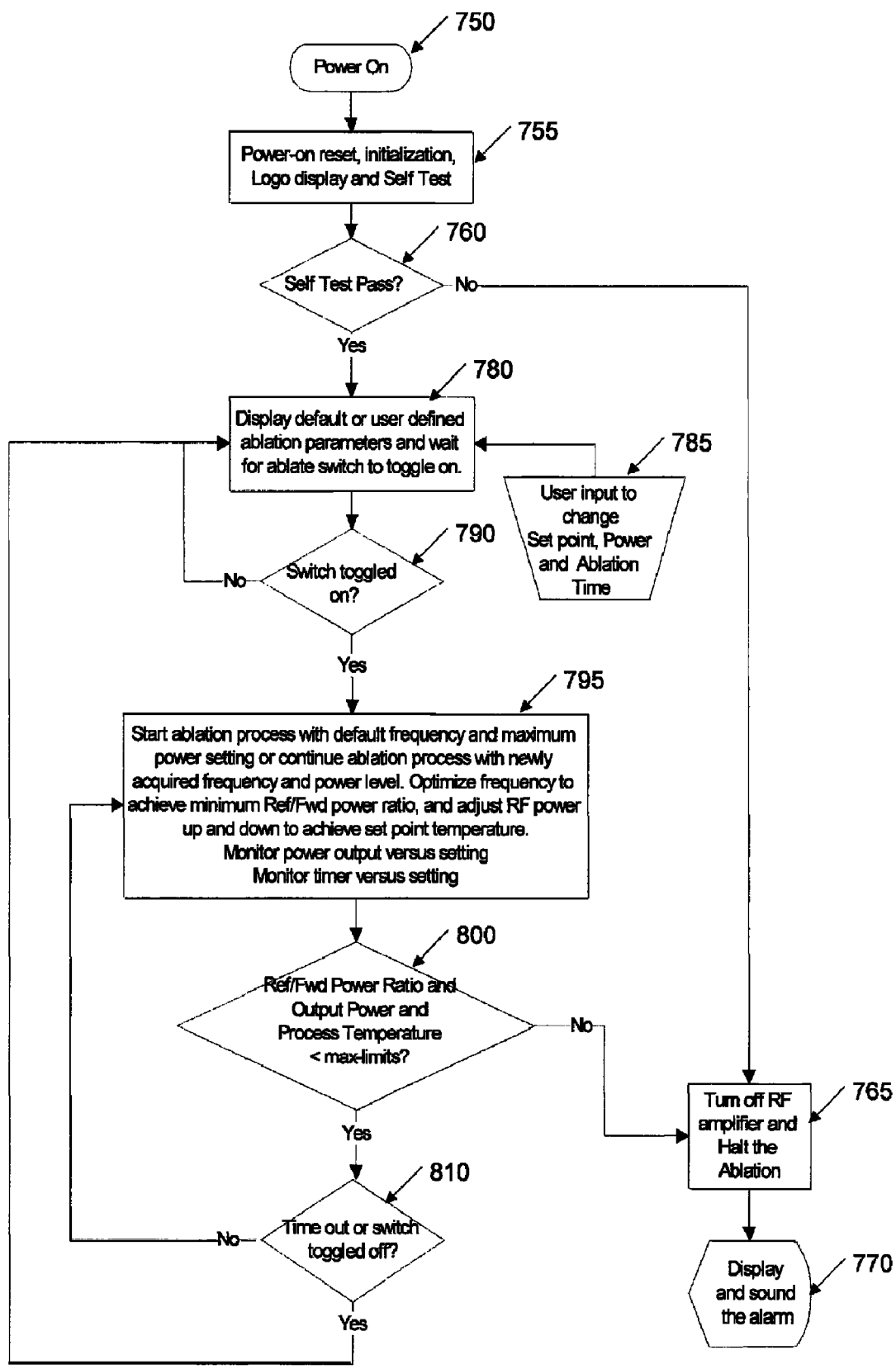
FIG. 12 is a schematic flow diagram illustrating a method of controlling an RF energy signal for use in an ablation system.

The coaxial cable device 20 has a flexible, elongated tubular body 32 having a proximal end portion 25 and a distal or tip portion 30. Located at the proximal end of the coaxial cable device is a handle unit 40 containing steering and positioning controls (not illustrated) for the coaxial cable device. An RF signal generator and system control unit or system 35 is connected to the proximal end of the coaxial cable device by cable 45, and is electrically coupled to the ablation device through the coaxial cable, as described in more detail below. The RF signal generator and control unit for controlling the RF signal delivered to the ablation device may be as described in co-pending application Ser. No. 11/479,259 filed on Jun. 30, 2006, the contents of which are incorporated herein by reference. One example of an RF signal control system is illustrated in FIGS. 12 and 13 and described in more detail below.

Figure 4:
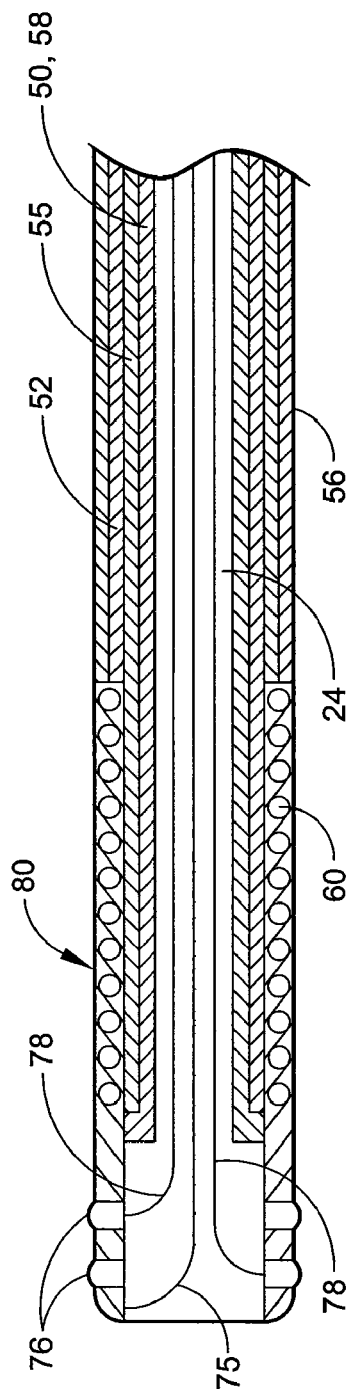
FIG. 4 is a partial sectional view of the distal end portion of a modified hollow conductive coaxial cable.

The structure of one embodiment of the coaxial cable device 20 is illustrated in more detail in FIGS. 2 to 4. The dimensions of coaxial cable device 20 are adapted as required to suit the particular medical procedure, as is well known in the medical art. The device 20 is generally tubular and has a multi-layer construction with a central bore or lumen 24 extending along its length. The distal end of the lumen 24 may be open as illustrated in FIGS. 2 to 4 or may be closed in other embodiments, for example as described below in connection with FIGS. 10 to 16.

The coaxial cable device comprises a first or inner electrically conductive tubular member or conductor 50 and a second, coaxial outer electrically conductive tubular member or conductor 52, a dielectric medium 55 between the conductors which electrically isolates the inner conductor from the outer conductor, and an outer jacket or casing 56 which encases the outer conductor 52 along the length of the coaxial cable device up to the distal tip portion 30. The outer casing 56 is generally constructed of a polymer material that is bio-compatible within the body vessel environment. Examples of such materials include thermoplastic elastomer material such as Pebax® available from Autochem Germany, polyethylene, polyurethane, polyester, polyimide, polyamide, and the like, with varying degrees of radiopacity, hardness, and elasticity.

The tubular body of the coaxial cable device may be formed with a plurality of segments using one or more of the aforementioned materials or equivalents, such that the device 20 is progressively more flexible towards its distal end. The segments may be joined together by thermal bonding, butt joints, or adhesive bonding. Braiding reinforcement may be provided to the surface of the tubular body to attain a desirable level of stiffness and torsional strength for the device to advance and negotiate through the body vessel of the patient, while still allowing the distal end portion to be bent when needed. The distal end portion 30 may be of a softer polymer compound than the remainder of the body, with little or no braiding or reinforcement, to provide the desired flexibility for distal deflection and shaping of the apparatus.

In one embodiment, the inner conductor 50 may be made of a flexible braided wire construction or thin film electrically conductive material. An inner liner or sleeve 58 of flexible dielectric material may be provided inside conductor 50 to surround the hollow central bore or lumen 24. The outer conductor 52 may be of a braided wire construction or may be a thin film electrically conductive material or the like. The sleeve 58, the inner conductor 50, and the dielectric medium 55 extend from handle unit 40 through the distal end portion of the coaxial cable device, while the outer conductor 52 and outer casing 56 extend from the handle unit 40 but terminate short of the distal end of the device, with the outer conductor projecting a short distance beyond the distal end of the outer casing, as seen in FIG. 2.

An ablation device 60 is located at the distal end portion 30 of the coaxial cable device 20 and is electrically coupled to both the outer coaxial conductor 52 at contact point 62 and to the inner conductor 50 at contact point 64. In turn, the first or inner conductor and the second or outer conductor are both electrically coupled to the RF energy source in unit 35. In the illustrated embodiment, the ablation device 60 comprises a helical coil wound around the outer circumferential surface of the coaxial cable device and extending from the end of the outer conductor 52 up to the distal end or tip of the device 20. The helical coil 60 is coated with an outer coating layer or end cap 65 of dielectric material such as a polymeric dielectric encapsulant which protects the structural integrity of the coil and also shields it from the surrounding biological environment. In alternative embodiments, other forms of ablation device or radio frequency antenna may be used in place of the helical coil antenna 60, such as a monopole bead antenna or a pair of spaced electrically conductive microstrips disposed at the distal end portion of the coaxial cable device, as described in U.S. Pat. No. 6,663,625 referenced above, the contents of which are incorporated herein by reference. The RF antenna 60 includes an electrically conductive material or wire strip that is wound in a helical fashion to form a helical coil. The appropriate diameter, pitch and length of the coil winding, and the selection of the conductive material or wire strip are a matter of choice, which can vary according to the particular procedure requirements as known in the art. Thus these design elements and considerations are not detailed here.

The RF antenna 60 is adapted to receive and radiate electromagnetic energy from a source of radio-frequency energy (not shown) in unit 35. An example of suitable spectrum of radio frequency is that of the microwave frequency ranging from approximately 300 MHz and up. The RF antenna is capable of applying substantially uniformly distributed electromagnetic field energy transmitted by the helical coil. The power of the electromagnetic field transmitted is substantially normal to the longitudinal axis of the RF antenna, and a uniform energy field is produced circularly about and bounded by the antenna. The energy delivered for the ablation is substantially uniformly distributed along the antenna, which is independent of the contact between the antenna and the tissue to be ablated.

In one embodiment, the coaxial cable device is optionally associated with a bending or shaping mechanism linked to handle 40 which bends or steers the distal end portion 30 of the device to conform to a body vessel or the like. This steering mechanism may be actuated by slide knobs as illustrated in FIG. 1, or by dials or the like in other embodiments. In FIGS. 2 and 3, steering is accomplished by means of a flexible guide or monorail member 70 which extends through the central lumen 24 up to the distal tip portion and is linked to a suitable actuator in the handle 40, for example in the manner described in U.S. Pat. No. 6,190,382, the contents of which are incorporated herein by reference.

Figure 11:
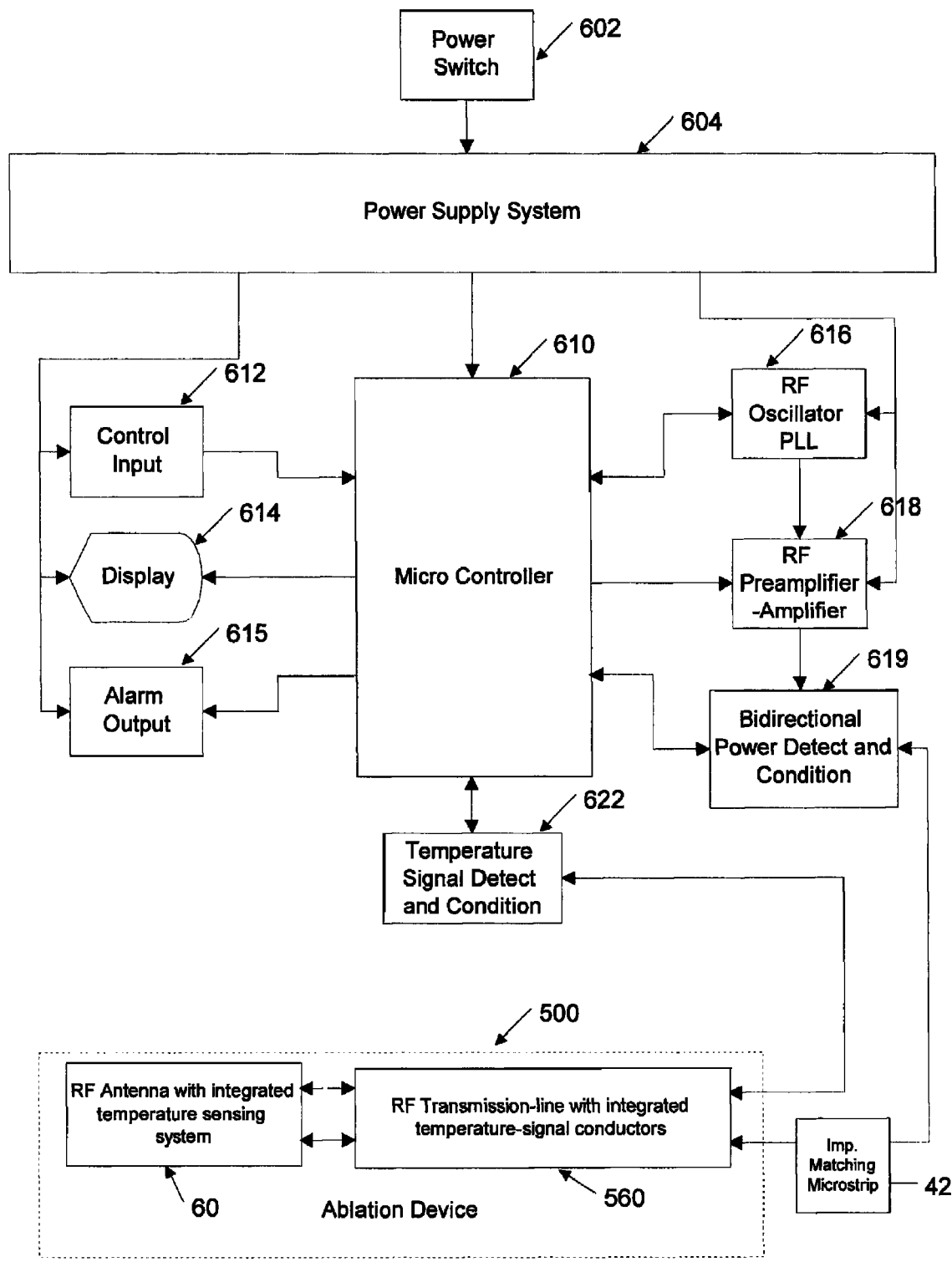
FIG. 11 is a schematic block diagram of a control system for controlling the RF energy signal delivered by a cable of the preceding embodiments.

In one embodiment, the inner conductor 50 and the outer conductor 52 of the coaxial cable device are terminated in handle or interface unit 40 with a coupling to respective junction plates of an impedance matching microstrip 42 as illustrated schematically in FIG. 11, and as described in U.S. Pat. No. 6,190,382 referenced above, the contents of which are incorporated herein by reference. The junction plates in turn are coupled to an electrical conductor of cable 45 which extends from the handle unit to the RF signal generator.

Figure 5:
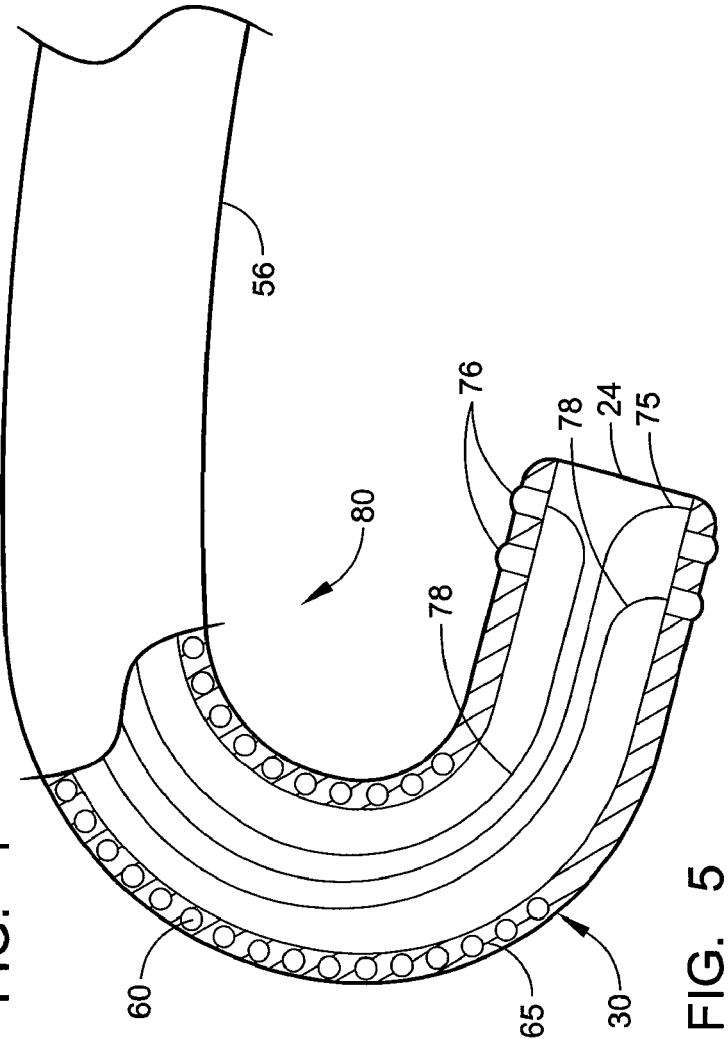
FIG. 5 is a partial sectional view similar to FIG. 5 illustrating the distal end portion deflected by one or more steering wires.

FIGS. 4 and 5 illustrate the distal end portion 80 of a modified cable 20, in which steering of the distal end portion is implemented by one or more pull wires 75 which extend through lumen 24 from the control handle 40 to the distal portion 80 of the coaxial cable device. In FIGS. 4 and 5, pull wire 75 is affixed to the inner wall of lumen 24 adjacent the distal end of device 80 by soldering or other suitable means. The distal end portion 30 may be pre-shaped so that it normally adopts a certain configuration or may be bendable. Pulling of wire 75 can bend the distal end portion 30 between the straight condition of FIG. 5 and the bent condition of FIG. 6. Gradual release of the wire can cause the portion 30 to adopt configurations between FIG. 6 and that of FIG. 5. The use of additional pull wires secured at different points around the distal end can provide for different directional movements.

In the modified coaxial cable device 80 of FIGS. 4 and 5, a pair of electrocardiogram (ECG) electrodes 76 are installed at the distal end portion of the coaxial cable device, forward of the RF antenna 60, and are connected to the control unit 35 by ECG wires 78 which also extend through the central lumen 24. The hollow central lumen therefore provides a passageway for wires and connectors through the cable. The structure of the coaxial cable device 80 is otherwise identical to that of the previous embodiment, and like reference numerals are used for like parts as appropriate.

Other types of bending or shaping mechanisms may be used in alternative embodiments for controlling bending of the tip or distal end portion of the coaxial cable device, and some alternative examples are described in detail in U.S. Pat. No. 7,004,938 of Ormsby et al. referenced above, the contents of which are incorporated herein by reference. However, it will be understood that any suitable mechanism may be incorporated in the catheter device in order to control the bending or steering of the tip portion as it moves through a body vessel, organ, or cavity.

FIGS. 6A and 6B illustrate another alternative steering mechanism for a coaxial cable device 20 which is identical to that of FIGS. 2 to 4 apart from the elimination of the monorail member 70 and the fact that the hollow central lumen 24 has a closed distal end or tip 90 rather than an open distal end as in the previous embodiments. In this embodiment, the closed distal end 90 is formed by a closed end of the outer coating layer 65 extending over the forward end of lumen 24. In this embodiment, the shape of the shapeable distal end portion 30 of the coaxial cable device 20 is regulated by a hydraulic or pneumatic fluid pressure instead of a deflection regulating member such as a shapeable internal element in lumen 24 and/or a pull wire or wires. In this embodiment, a hydraulic or pneumatic pressure source (not illustrated) is connected by a valve to the lumen 24 at a proximal end of the device 20.

In FIGS. 6A and 6B, the multi-layer coaxial cable structure 56, 52, 55, 50, and 58 is shown schematically as a single layer 105 for convenience, but the structure of multi-layer 105 is identical to the multi-layer tubular wall structure described above in connection with FIGS. 2 and 3. In this embodiment, rather than using a pre-shaped deflection member as in previous embodiments, the tubular wall of the coaxial cable device 20 in the distal end region 90 may itself be pre-shaped to adopt a bent configuration, as illustrated in FIG. 6A. In order to straighten the distal end portion 90 to the straight configuration illustrated in FIG. 6B, fluid (gas or liquid) may be injected into the lumen 24 so as to fill the lumen, as indicated by the arrows. This causes pressure to be applied to the wall of the distal end portion, straightening the distal end portion. The straight configuration may be maintained by closing the supply valve. In order to move the distal end portion into a non-straight configuration, the valve may be opened to allow at least some of the fluid to escape from lumen 24, with the amount of bend determined based on the amount of fluid escaping, so that any configuration between the two extremes of FIGS. 6A and 6B may be adopted.

FIGS. 7A to 7C illustrate the distal end portion 150 of another embodiment of coaxial cable device 20 adapted for insertion into a body vessel or cavity. FIGS. 7A to 7C illustrate only a distal end portion, but the coaxial cable device is of suitable length to extend to a desired location in the body and to connect to a handle/steering control unit 40 and signal control unit 35 in a similar manner to coaxial cable device 20 of FIG. 1. As in the previous embodiments, device 150 has hollow coaxial inner and outer electrically conductive members or conductors 640, 660 separated by a dielectric medium 650 which may comprise any suitable dielectric and which insulates the conductors from one another. A central lumen or hollow bore 520 extends through the coaxial cable device, as in the previous embodiments.

As in the previous embodiments, the outer conductor 660 may be covered by an outer layer 670 of non-conductive material. As in FIGS. 2 and 3, outer conductor 660 terminates short of the distal end 690 of the coaxial cable device, and an ablation device such as an RF antenna in the form of a flexible helical coil 620 of conductive material is mounted over the projecting distal end portion of device. The outer layer 670 of non-conductive material extends forwardly from outer conductor 660 to cover and protect the helical coil 620. Outer layer or jacket 670 helps to provide electromagnetic and thermal isolation from the surrounding biological environment.

The helical coil and inner and outer conductors may be of conductive metallic or conductive polymer material, depending on the application and flexibility requirements. In this embodiment, as in the previous embodiments an inner tubular liner or sleeve 630 of flexible material extends inside the inner conductor 640 from the proximal to the distal end of the coaxial cable device. Sleeve 630 is constructed of a dielectric material, which reduces the likelihood of an electrical short between the metallic or conductive surfaces of the helical coil and the body fluids in lumen, and also helps to confine the electromagnetic field to the outside of the lumen.

Helical coil 620 is electrically coupled to the distal end of the first conductor 640, and is also electrically coupled to the distal end of the second conductor 660, and the conductors are coupled in turn to a source of RF energy in the manner described above in connection with FIGS. 1 to 4.

The coaxial cable device is formed in an elongated tubular configuration with inner and outer tubular conductors 640, 660 arranged in a substantially coaxially and circumferentially aligned relationship with each other to form a hollow cable which extends from the helical coil 620 proximally to the handle 40 for the delivery of RF energy. This configuration is advantageous because the tubular conductors 640, 660 (which may be helically coiled) and the helically coiled antenna 620 maximize the electrically conductive surface area, and, hence, efficiency of the microwave energy delivery, while providing a central coaxial lumen 520 which may be used to accommodate a guide for shaping the distal end portion of the coaxial cable device, a pull wire or wires, or a fluid such as gas for steering and shaping purposes, as described above in connection with FIGS. 7 and 8. Although the lumen 520 is shown coaxial with the conductors 640, 660, in an alternative embodiment, one or more axially extending lumens may be provided, one or more of which may not be coaxial with the conductors 640, 660.

In any of the foregoing embodiments, alignment of the coaxial cable device with the desired tissue ablation pathway may be facilitated with the use of one or more radio-opaque markers and intracardiac electrodes mounted in the distal end portion of the device.

In the embodiment of FIGS. 7A-7C, an elongated flexible spine 680 extends through lumen 520 from the handle, with a distal end portion 690 of the spine including a distal atraumatic tip 700. The distal end portion 690 may be secured to a distal portion of the antenna 530, at the distal end of the coaxial cable device 150, so that the atraumatic tip 700 is adjacent to the antenna 530. The tip 700 is atraumatic to reduce the potential for perforating a body vessel. Optionally, the atraumatic tip 700 is formed of radio-opaque material to support identification of the location of the antenna 620 during administration of the ablation procedure.

The spine 680 is made of one or more spring-like flexible materials. By way of example, in one embodiment of the invention, the spine 680 is made of stainless steel. In another embodiment of the present invention, the spine 680 is constructed of a plurality of elongated members having pre-defined dimensions and joined to form a unitary body. The proximal portion of the spine 680 may be secured to a slide control mechanism (not illustrated) in the handle 40.

In an additional embodiment of the spine 680, at least the distal end portion 690 of the spine 680 may be more flexible than remaining portions of the spine 680, i.e., the spine 680 may have variable stiffness along at least part of its length. This difference in flexibility can be effected by varying the shape and the size of the cross-sectional profile of the spine 680. In a further embodiment of the spine 680, at least the distal end portion 690 of the spine 680 may be made of a bi-metal or shape-memory alloy ("SMA") material such as the nickel-titanium alloy sold under the trademark nitinol. Alternatively, the entire spine or a larger portion of the spine 680 than the distal end portion 690 may be made of such SMA material. The use of SMA material enables pre-shaping of the distal portion 540 of the coaxial cable device to conform the body of the coaxial cable device to attain a desired curvilinear profile, thus facilitating the navigation and placement of the coaxial cable device to the internal contour or geometry of the body vessel. Means and methods for pre-shaping of SMA materials are generally known in the art and are not discussed in detail here.

Optionally, one or more intracardiac electrogram (ECG) electrodes may be mounted on or within the distal end portion of the coaxial cable device and connected by cables extending through lumen 520 to a suitable ECG monitor included in control unit 35. This can help in positioning the RF antenna for ablation purposes.

FIGS. 8 and 9 illustrate the distal end portion 160 of another embodiment of a coaxial cable device which extends to a proximal end portion (not illustrated) connected to a handle and to a control unit such as the control unit 35 of FIG. 1. The distal end portion 160 is similar to that of FIGS. 6A and 6B and like reference numerals are used for like parts as appropriate. As in FIGS. 6A and 6B, the multi-layer coaxial cable structure in FIGS. 8 and 9 is shown schematically as a single layer 105, but may be identical to the multi-layer structure of FIGS. 2 to 5, with inner and outer coaxial tubular conductors separated by a dielectric medium. A temperature sensor 710 is located in the distal end portion of the lumen 24 close to the distal tip 90. The temperature sensor 710 may be a thermistor, thermocouple, or the like, and has a pair of conductor wires 720 extending from the sensor through the lumen 24 to the proximal end of the coaxial cable device, where they are connected to control circuitry in an RF signal control unit. One or more ECG electrodes (not illustrated) may also be located in the distal end portion 160 of the cable, as in the previous embodiment, and may be connected to wires which extend through the lumen to the proximal end connector of the cable for coupling to an ECG monitor.

Any suitable steering mechanism may be incorporated in the coaxial cable device of FIGS. 8 and 9 for moving the distal end portion between the straight and curved configurations illustrated in these drawings, as described above in connection with the preceding embodiments. FIGS. 8 and 9 illustrate one possible example of such a mechanism in which the distal end portion 160 is of suitably pre-shaped material or is otherwise biased so that it normally adopts the straight configuration of FIG. 8. In this example, deflection and shaping of the shapeable distal end portion is controlled by a deflection member 180 extending through a deflection regulating member or tube 190 which extend through the lumen 24 from the proximal end portion or handle/deflection control unit to the distal portion 160 of the coaxial cable device. The handle or deflection control unit has a suitable controller for moving the deflection member 180 between the retracted position of FIG. 8 to the extended position of FIG. 9 where it extends to a location close to the distal end tip 90 of the device. The deflection member 180 is pre-shaped to adopt a curved configuration as in FIG. 9 when extended out of the rigid tube 190, and therefore bends the distal end portion 160 to adopt a similar curvature. This mechanism may be used to enable an operator to shape or deflect the distal end portion between the straight configuration of FIG. 8 and the bent configuration of FIG. 9, or any configuration therebetween by partially or fully extending the deflection member 180 from the regulating member or tube 190. This is just one example of a deflection or shaping mechanism, and other arrangements may be used in alternative embodiments, such as supplying a fluid to the central lumen 24 as in FIGS. 7A and 7B so as to deflect the distal end portion from a bent configuration to a straight configuration, or vice versa, or deflecting the distal end portion by means of pull wires or the like.

Figure 10:
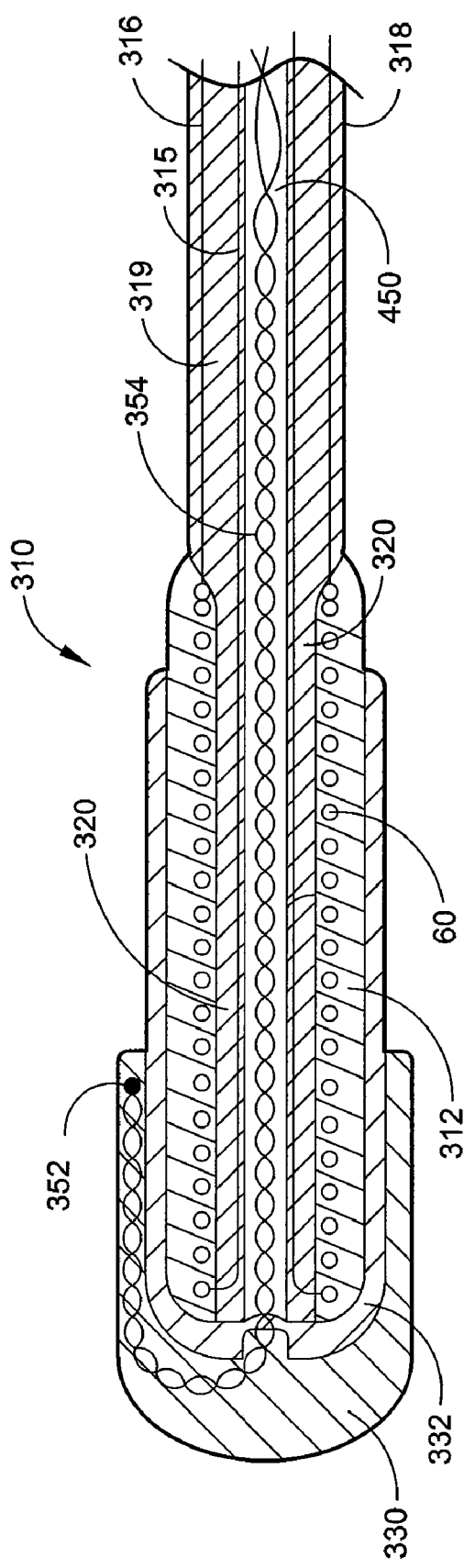
FIG. 10 is a cross-sectional view of the tip or distal end portion of another embodiment of a coaxial cable incorporating electrocardiogram (ECG) electrodes and a temperature sensor.

FIG. 10 illustrates the distal end portion 310 of a modified coaxial cable device having integrated electrodes 312, 330 separated by dielectric or non-conductive polymer layer or sleeve 332. In one embodiment, the electrodes are ECG electrodes, although they may be other types of electrodes in other embodiments. Although two electrodes are illustrated in FIG. 10, in other embodiments one electrode or more than two such electrodes may be provided. In the embodiment of FIG. 10, a pair of coaxial inner and outer tubular conductors 315, 316 extend along the length of a tubular body 318 which extends from a proximal end of the device, for example at a handle and steering unit 40 as in the previous embodiments, up to the distal end of the device. The outer conductor 316 is connected to the proximal end of RF antenna 60 and the inner conductor 315 is connected to the distal end of the RF antenna adjacent the tip of the coaxial cable device. The structure of the remainder of the tubular body 318 which is not shown in FIG. 10 may be identical to that of the tubular bodies of the coaxial cable devices described above, and a suitable connector (not illustrated) may be provided at the proximal end of the coaxial cable device for connecting the conductors 315, 316 to a suitable RF source and the electrodes 312, 330 to a suitable ECG monitor. The distal end portion 310 illustrated in FIG. 10 may be shapeable or bendable in a similar manner and using the same or similar control devices as were described above in connection with FIGS. 1 to 9.

In the embodiment of FIG. 10, the tubular body 318 is of a non-conductive polymer and has a portion 320 of reduced outer diameter at its forward end. The first electrode 312 comprises a sleeve of flexible conductive material mounted over the reduced diameter end portion 320 of the tubular body. The RF or microwave antenna 60 is embedded in the sleeve or electrode 312. The tubular inner and outer conductors 315, 316 extend through the tubular body 318 as illustrated for connection to the opposite ends of the antenna coil 60, with a dielectric medium 319 between the conductors. A central hollow lumen or bore 450 extends through the coaxial cable device inside the inner electrode. An outer cover layer 332 of non-conductive material extends over the distal end of lumen 450 and rearwardly over at least part of electrode layer 312. The second electrode 330 comprises conductive tip or cap mounted over the end of the coaxial cable device. Electrode 330 is also made of flexible conductive material. The two electrodes may be secured over the inner tubular body 318 by adhesive, bonding, mechanical force, heat sealing or the like. The flexible conductive material forming the electrodes is at least substantially non-metallic material and may be a conductive polymer material which is sufficiently bendable to allow bending of the distal end portion 310 to follow the contour of a body vessel, for example.

A pull wire (not illustrated) may extend through the lumen 450 to the tip of the device for operation by suitable steering and positioning controls (not illustrated) at the proximal end of the coaxial cable device, for controlling bending of the distal end portion. Such a pull wire mechanism is described in U.S. Pat. No. 7,004,938 referenced above, the contents of which are incorporated herein by reference.

The embodiment of FIG. 10 also includes a temperature sensor 352 embedded in the conductive tip electrode 330 adjacent the tip of the coaxial cable device. In the illustrated embodiment, the temperature sensor may be a thermistor, thermocouple, or the like and has a thermocouple junction or sensor end 352 and a pair of braided wires or conductors 354 extending from the sensor 352 through the tubular body to the connector at the proximal end of the coaxial cable, where they are connected to control circuitry for monitoring the temperature at the distal end of the coaxial cable device and controlling the antenna operation, as described in co-pending application Ser. No. 11/479,259 referenced above, the contents of which are incorporated herein by reference. The electrodes may be ring-shaped or annular band electrodes in alternative embodiments, or may have other alternative configurations, such as those described in co-pending application Ser. No. 11/479,259.

In FIG. 10, the thermocouple wires 354 have the dual function of providing a temperature sensor output as well as providing an ECG monitor output in combination with outer antenna conductor 316. The ECG output may be measured between conductor 316 and either one of the thermocouple wires 354. The temperature output may be used in monitoring and controlling operation of the RF antenna, as described below in connection with FIGS. 11 and 12.

In FIG. 10, electrodes are mounted at the distal end portion of a shapeable or bendable hollow coaxial cable device to allow physicians to locate a tissue region causing problems and to obtain both optimum tissue proximity and electrical conductive activities before and after ablation, as well as to obtain feedback of their actions. Similar electrodes may provided at the distal end portion of any of the coaxial cable devices described above in connection with FIGS. 1 to 9. Although two electrodes are provided in these embodiments, only one electrode or more than two electrodes may be provided in other embodiments. The electrode or electrodes in these embodiments may be ECG or other types of electrodes. Radio-opaque markers (not illustrated) at the distal end portion of the coaxial cable device may also be used to aid in positioning the tip of the coaxial cable device. Where the electrodes are ECG electrodes, the conductor wires connected to the electrodes and to the proximal end connector of the coaxial cable device communicate with an external ECG system and monitor (not illustrated) via a suitable connection cable which transmits ECG signals between the electrodes and ECG system. The antenna conductors and thermocouple wires (if a temperature sensor is present) are similarly connected to an appropriate antenna output control system.

The electrodes in FIG. 10 are made of a suitable flexible conductive material, so that they can bend with the remainder of the distal end portion during steering. Such electrodes avoid or reduce the problems encountered with metallic electrodes, since they do not absorb microwave energy to any great extent and do not become excessively hot. The electrodes may be of an at least substantially non-metallic material, and in one embodiment they are made from a conductive polymer material such as nylon, polyethylene, polyolefin, polypropylene, polycarbonate, Pebax®, TPE (thermoplastic elastomers) and blends, loaded with a selective conductive material. Other non-conductive parts of the coaxial cable device may be of the same polymer material or different polymer materials. The conductive material may be micro-carbon spheres, carbon particles, carbon nanotubes, nickel dust, or the like. The electrodes may be made entirely of conductive polymer material or may be a mixture of conductive and non-conductive polymer material, or a mixture of conductive and non-conductive materials with metal substrates. The composite polymer material is selected to have a relatively low resistance for reduced interference with the microwave radiation pattern, and to be hydrophilic for improved wetability on the outer surface of the coaxial cable device.

Heat energy, adhesives, and/or mechanical force may be used to laminate the conductive and non-conductive polymer layers in the embodiment of FIG. 10, or any of the preceding embodiments. Metallic substrates may also be laminated between the polymer layers, such as the inner and outer tubular conductors which provide power for operating RF antenna 60.

A suitable control system for monitoring and controlling operation of an RF ablation antenna, such as the antenna incorporated in the coaxial cable devices of the preceding embodiments, is schematically illustrated in FIGS. 11 and 12. This system is also described in co-pending application Ser. No. 11/479,259 filed on Jun. 30, 2006, the contents of which are incorporated herein by reference.

As illustrated in FIG. 11, the control system has a power switch 602, power supply system 604, micro-controller system 610, RF signal generator or oscillator 616, RF amplifier 618 comprising a pre-amplifier, RF bi-directional coupler 619, control input 612, display 614, and alarm output 615. The bi-directional coupler 619 is connected to the proximal end of the coaxial cables or electrodes 560 in a coaxial cable device of any of the previous embodiments, which form an RF transmission line. An RF antenna 60, which may have an integrated temperature sensor, is located at the distal end of the coaxial cable device, as in the preceding embodiments. In one embodiment, coaxial cable 560 may be identical to the coaxial cable devices of any of FIGS. 1 to 10, and the antenna may be the coiled RF antenna 60 of these embodiments. Where the system includes temperature sensing, leads connected to the temperature sensor are connected at their proximal ends to temperature signal detection and conditioning module 622, which in turn is connected to micro-controller 610.

The RF ablation system is powered by ordinary alternating current power and it could be adapted to be powered by an appropriate direct current source as well. The power switch 602 connects the electrical power to the system power supply 604. The system power supply provides primary patient safety isolation and synthesizes various direct current voltages necessary to operate the apparatus to effect tissue ablation.

The microcontroller 610, which is microprocessor based, provides for user input, displays for inputs and outputs, and sets system alarm conditions. Microcontroller 610 also monitors and controls RF power synthesis and communication to the RF antenna 60 and ablation tissue. As shown in FIG. 11, the microcontroller 610 monitors and controls RF signal oscillator 616, which receives power from the power supply system 604. RF signal oscillator generates a continuous RF frequency wave signal at a power level and frequency determined and controlled by micro controller 610.

In the embodiment of FIG. 11, the RF signal oscillator 616 is electrically coupled to the power amplifier 618. The power amplifier 618 includes a preamplifier, which initially amplifies the wave signal from the RF generator and produces a first train of relatively low energy pulses. After amplification by RF amplifier, the energy pulses are then delivered via a transmission line or coaxial cable 560 to an RF antenna 60, which is placed within or adjacent body tissues or vessels in the proximity of the tissue to be ablated.

As shown in FIG. 11, the bi-directional coupler 619 is electrically interposed between the amplifier 618 and transmission line 560. The coupler samples the relatively low energy forward pulses along the transmission line and the energy pulses reflected from the target ablation tissue and uses the signal samples as feedback to the micro controller 610. The feedback mechanism provided by sampling the signal at the coupler 619 is useful for scaling back the amount of reflected energy. Too much signal reflection could potentially destroy sensitive system components or cause patient injury.

Electrically in communication with the bi-directional coupler 619, the micro-controller 610 monitors the forward and reflected energy pulses. Micro-controller 610 then defines a ratio for the reflected and forward energy pulses. In one embodiment, this ratio comprises a voltage standing wave ratio (VSWR), computed as:

$$VSWR = \frac{1 + |\Gamma_0|}{1 - |\Gamma_0|}$$

where $\Gamma_0$ represents the load reflection coefficient computed using the appropriate boundary conditions along RF transmission line 560.

A low ratio would indicate that most of the energy generated by the system is applied to the load for ablation, and is characteristic of having achieved matched impedance between the apparatus and the ablation load. A high ratio, on the other hand, would indicate that a significant amount of the energy generated by the system is being reflected, and is characteristic of a high degree of return loss, or leakage, resulting from a poor impedance match.

To the extent that the impedance of RF transmission line 560 is affected by the RF energy pulse frequency, one embodiment provides a means to enable the change of frequency in the power output of the system such that both the line impedance and the load impedance will be matched. The means for sensing (i.e., the bi-directional coupler, in one embodiment) and the means for adjusting comprise a means for adjusting RF signal source 616 and RF power amplifier 618 in response to the means for controlling (i.e., the micro controller 610) to match the transmission line impedance to the load impedance. For example, if the ratio indicates that too much energy is being reflected (e.g., VSWR is high), the micro controller 610 adjusts the frequency of the RF signal generated by the oscillator 616 to effect a reduced value in the ratio of the reflected and forward energy pulses. Such a reduction in the power ratio effects impedance matching between the transmission line and the ablation load. An acceptable amount of return loss would depend upon the application. However, since a perfect impedance match is never achievable, micro controller 610 can allow for the user to adjust the frequency such that the ratio drops below some threshold value. The threshold value may be below 1.4:1, and in one embodiment the threshold value is 0.4:1.

Because load impedance can vary widely among tissue types and can vary according to the quality and quantity of fluids surrounding the tissue, such as in a blood-filled cavity or chamber, the control system supports a broad range of frequency adjustment settings to enable flexible deployment of the ablation system in the field.

Having achieved a match in the impedance, the microcontroller 610 adjusts the power amplifier 618 to produce the train of relatively high energy pulses, which will be delivered via the transmission line to the RF antenna to effect tissue ablation. In one example of the present invention, the power level generated for ablation process was approximately 60 watts.

In addition to providing monitoring and adjusting functions over the frequency of the RF pulses, the micro-controller 610 also communicates the various signals and indicators to a user such as electro-physiologist. The system supports manual override in the RF frequency, output power, and setting the ablation duration. In a typical configuration, the control input 612 of the present invention may be equipped with a multi-line display, a set of up and down keys for adjusting output power level and ablation period, an ablation on/off key for activating ablation processes, and a mode/setup key for changing display mode and/or configuring an I/O port.

The output power level of the RF amplifier 618 is monitored continuously during ablation processes. The RF bi-directional coupler 619 provides the ability to sample both forward and reverse power levels at attenuated levels that are electrically connected to the micro-controller assembly. The micro-controller assembly compares the two signals and adjusts both the signal source and the preamplifier/power amplifier gains to achieve lowest reverse-to-forward power ratio.

In one embodiment, the RF based catheter system optionally monitors and controls the microwave frequency and power output within a range of about 900 MHz to 930 MHz to minimize reflected-to-forward power ratio. The RF antenna may be manufactured and tuned to 915 MHz in a saline solution closely approximating biological tissue and fluid filled animal body vessel to be ablated. When in the vicinity of the biological tissue to be ablated, the electrical dimension of the RF antenna 60 may slightly altered temporary to cause reflected power to increase. Increased reflected power reduces overall power available for irradiation and therefore, reduces efficient tissue ablation. If the reflected power is left unchecked and increases greatly, local heating of the RF antenna 60 may occur and produce unwanted ablation affects.

In addition to monitoring forward and reflected energy pulses, in one embodiment the microcontroller is also programmed to monitor the temperature detected at a temperature sensor at the distal end of the coaxial cable device, which is closely related to the temperature induced in the tissue as a result of the ablation process, since the temperature sensor is located close to the ablation site. It will be understood that temperature sensor may be mounted on the outside surface or at the tip of the distal end of the coaxial cable device in alternative embodiments.

In the embodiment of FIGS. 11 and 12, the microcontroller 610 is programmed to adjust the frequency to achieve a minimum reflected to forward power ratio and to adjust the RF power level to achieve a selected temperature setting. The temperature setting may be a temperature set point, plus or minus a few degrees, or may be a selected temperature range, as described in more detail below in connection with the flow diagram of FIG. 12. The reflected power is proportional to the combined impedance of the biological tissue and the antenna system as a whole, and therefore minimizing the reflected power is the same as impedance matching the system for maximum transfer of forward power for delivery to the tissue being ablated. At the same time, the temperature changes that are measured by the temperature sensor can be correlated to the combined RF energy effect (ablation) of the biological tissue and the antenna system as a whole. By establishing the set points of the temperature as measured and adjusting the RF frequency and the power delivered to the target tissue within the preset temperature set points, one can provide an efficient and effective means for tissue ablation. Although this embodiment uses both the detected temperature and reverse to forward power ratio as control parameters in adjusting the RF signal parameters in order to achieve a temperature and a power ratio close to user or default settings, alternative embodiments can use temperature alone or the reverse to forward power ratio alone as the control parameter. The microcontroller may also monitor the output power and temperature to ensure that they do not exceed maximum limits for safe operation.

In the system of FIGS. 11 and 12, the microcontroller adjusts the RF frequency by controlling oscillator 616, thereby also adjusting the reflected/forward power ratio. RF power delivered can be adjusted up and down by controlling amplifier 618, in turn adjusting the reflected temperature. The flow diagram of FIG. 12 illustrates the steps in an ablation procedure according to an embodiment of the invention, using the control system of FIG. 11 along with an RF ablation system incorporating a temperature sensor, for example as in FIGS. 8 and 9 or FIG. 10. The power is first switched on at switch 602 (step 750) and a power on reset, initialization, and self-test procedure is then carried out (step 755). In this step, the system runs a battery of initialization routines in order to establish system integrity, as described above in connection with step 401 of FIG. 5. If the self test fails (condition block 760), the RF amplifier will be turned off and the ablation procedure will be halted (step 765), and the alarm will be displayed and sounded (step 770). If the self test is successful, the default or previous user selected parameters will be displayed on display module 614, and the system will wait for the user to toggle on an ablation switch before starting the ablation process (step 780).

Ablation parameters can be adjusted or set by an operator at input module 612 at the start of an ablation procedure (step 785). The parameters which can be varied by the operator are a temperature set point, power level, frequency, and an ablation time period. The desired parameters will vary depending on the targeted biological tissue and other factors. The system will include default starting values of frequency and power level, and both will be adjusted as necessary to achieve the lowest possible reverse/forward power ratio and a process or detected temperature at the temperature sensor close to the temperature set point. In addition to the pre-set or operator selected operating power level, temperature level, frequency, and ablation time period, the system also has fixed maximum limits of power ratio, power and temperature for safe operation which are independent of the control loop. The maximum power ratio, power level and temperature represent the maximum limit that the catheter can withstand, for safe operation of the system.

As noted above, the operator can vary the set point temperature or temperature range, power level, frequency, and ablation time period by changing the settings on the control input 612 at step 785. The temperature setting input by an operator may be a specific temperature or a temperature range. Where the input is a specific temperature, the system controls the RF signal pulses so that the detected temperature is equal to the specific temperature selected by the operator, plus or minus a few degrees. Where the input is a temperature range, the system controls the RF signal pulses so that the detected temperature is within the selected range. The set point temperature or temperature range selected may be within the range from 45 degrees Celsius to 125 degrees Celsius, and the exact temperature setting will depend on the targeted biological tissue. For example, in the heart, the temperature setting or set point may be in the range from 50 to 90 degrees Celsius. In non-intracardiac tissue, such as the liver, outer surface of the heart, or other non-intracardiac tissue regions, the temperature setting or set point may be in the range from 60 to 120 degrees Celsius, for example. The system may have recommended temperature levels or ranges for different types of biological tissues for operator reference purposes. In step 795, the microcontroller will vary the RF frequency to achieve and maintain the lowest possible reverse/forward power ratio and adjust the RF power level up or down from the set point to achieve a temperature at or close to the set point or within the set point range (where the temperature setting is a range rather than a specific temperature). At the same time, the power output, temperature and timer is monitored and compared to the settings and to the system maximum limits for output power and process temperature.

As noted above, it is desirable for tissue ablation purposes to match the transmission line impedance as closely as possible to the load impedance. If the ratio of reverse to forward or input power is too high, it indicates that too much energy is being reflected, i.e. not being absorbed by the tissue, and the signal frequency is adjusted to produce a reduced power ratio. Because a perfect impedance match is not likely in practice, the frequency and power level are adjusted by the microcontroller in step 795 to achieve the lowest possible level within the constraints of the selected ablation temperature set point. As in the previous embodiment, a threshold level for the ratio may be set, such as 0.4:1, and the controller can then adjust the frequency until the ratio drops below this value. In an alternative embodiment, as noted above, the power ratio is not used and the system controls the frequency and power level of the RF signal to maintain the selected temperature setting.

In the illustrated embodiment, the RF frequency and power level are varied in order to achieve a temperature as close as possible to the selected temperature set point while maintaining a desired ratio of reflected to forward power. The detected temperature at the temperature sensor is indicative of the combined RF energy effect on the biological tissue. Controlling the temperature to be at or close to a set point may therefore improve or optimize tissue ablation.

As noted above, the system has maximum limits set for the power ratio, power level, and temperature level, and will stop the ablation process if any of these limits is exceeded (step 800). In the event that one of the maximum limit values is exceeded, the RF amplifier is turned off and the ablation process is halted (step 765) and, in step 770, the system displays and sounds the alarm 615. As long as the power ratio, power level and temperature are within the maximum limits, the ablation process continues for the pre-set time period or until the ablation switch is toggled off (step 810). When the ablation time period expires or the ablation switch is turned off by the operator, the system returns to step 780, displaying the default or previous user defined ablation parameters and awaiting further input by the user or operator.

FIGS. 11 and 12 illustrate a control system and method which continuously monitors forward power, reflected power and temperature and adjusts both frequency and power levels to achieve and maintain lowest possible reflected/forward power ratio for impedance matching, combined with near set point temperatures. The frequency and power level are set by micro-controller and firmware adjustment of the RF oscillator frequency and output level fed to the preamplifier-amplifier module 618. An ablation process starts with default values of frequency and power level and both are adjusted as necessary to achieve lowest ref/fwd power ratio and process temperature close to set point temperature. The system also has maximum limits for the power ratio, power level and temperature independent of the control loop and halts the process and alarms the user if the monitored readings exceed them.

The outer dimensions of the body of the coaxial cable device in each of the above embodiments may be adapted as required to suit the particular medical procedure, as is well known in the medical art. In one embodiment, the device is used to ablate cardiac tissue. However, the device may be used to ablate other types of body tissue in different organs, both internal and external to the body. The tubular body of the coaxial cable device may be generally constructed of a polymer material which is bio-compatible with the body vessel environment.

In each of the above embodiments, the ablation device or RF antenna is adapted to receive and radiate electromagnetic energy in order to treat a selected biological tissue site by changing a property of the biological tissue at the site. An example of a suitable spectrum of radio frequency energy for use in tissue ablation is that of the microwave frequency range above 300 MHz. The RF antenna is capable of applying substantially uniformly distributed electromagnetic field energy along the RF antenna in a direction substantially normal to the longitudinal axis of antenna 60. The elongate, flexible coaxial cable device connected to an RF source and control unit at its proximal end extends to a distal end portion at which the RF antenna is mounted. The coaxial cable device in each of the foregoing embodiments has coaxial inner and outer conductors extending from its proximal end and separated by a dielectric medium, and a central lumen or bore inside the inner conductor extends the length of the coaxial cable device and can be used to accommodate conductor wires which are connected to ECG electrodes, temperature sensors, or the like, as well as a suitable shaping or steering mechanism for controlling the shape or deflection of the distal end portion of the coaxial cable device in which the RF antenna is located.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are, therefore, representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A hollow coaxial cable device adapted for transmission of radio frequency (RF) energy for the ablation of biological tissue, comprising:
    an elongate cable adapted for placement adjacent to or within biological tissues and vessels, the elongate cable having a proximal end and a distal end and comprising inner and outer conductors extending substantially the entire length of the elongate cable from the proximal end to a distal end portion of the elongate cable;
    the inner conductor comprising a first elongated electrically conductive tubular member having a hollow, axially extending lumen and an outer surface;
    the outer conductor comprising a second elongated electrically conductive tubular member disposed in a substantially coaxial relationship over at least a portion of the inner conductor and having an inner surface spaced from the outer surface of the inner conductor to define an annular space between the inner and outer conductors;
    a dielectric medium disposed in the annular space and extending between the inner surface of the outer conductor and the outer surface of the inner conductor;
    a radio frequency (RF) antenna connected to distal end portions of the inner and outer conductors and projecting forwardly from a distal end of the outer conductor, the RF antenna being configured to deliver radio frequency energy to body tissue disposed at the distal end portion of the elongate cable;
    a pre-shaped deflection member located within the distal end portion of the elongate cable and movable for changing a configuration of the distal end portion of the elongate cable between straight and curved configurations, the pre-shaped deflection member extending through the hollow, axially extending lumen to the distal end portion of the elongate cable; and
    a temperature sensor located at the distal end portion of the elongate cable within the hollow, axially extending lumen, the hollow, axially extending lumen having a central longitudinal axis, the deflection member extending along the central longitudinal axis, and the temperature sensor being offset from the central axis and having signal wires extending from the temperature sensor alongside the deflection member and up to the proximal end of the elongate cable.

2. The device of claim 1, wherein the pre-shaped deflection member is extendible between a retracted position spaced from the distal end of the cable and an extended position in which a forward end portion of the deflection member extends up to a location adjacent the distal end of the cable and past the temperature sensor, the deflection member being straight in the retracted position and the forward end portion being curved in the extended position.

3. The device of claim 1, wherein
    the dielectric medium comprises a dielectric layer between the inner and outer conductors having a projecting forward end portion which projects forwardly from the distal end of the outer conductor; and
    the RF antenna comprising a helical coil wound circumferentially around an outer surface of the projecting forward end portion of the dielectric layer and.

4. The coaxial cable device of claim 1, further comprising at least one electrode disposed at the distal end portion of the cable.

5. The device of claim 4, further comprising a conductive wire extending from the at least one electrode through the hollow, axially extending lumen to the proximal end of the cable.

6. The device of claim 4, wherein the at least one electrode is an electrocardiogram ("ECG") electrode.

7. The device of claim 4, wherein the at least one electrode is comprised of an electrode material that an at least substantially non-metallic material.

8. The device of claim 7, wherein the at least one electrode is comprised of an electrode material that a flexible conductive polymer material.

9. The device of claim 1, further comprising an RF signal generator connected to the RF antenna which generates a train of RF energy pulses which is transmitted to the RF antenna, a detector which detects a reflected signal and a forward signal of the train of RF energy pulses when the RF antenna is adjacent to a biological tissue site to be ablated, a controller which communicates with the detector and RF signal generator, the controller having a processing module which determines a voltage standing wave ratio (VSWR) based on the reflected signal and forward signal, and an RF signal adjustment module which adjusts a frequency of the train of RF energy pulses based on the VSWR to effect a substantial match of a coaxial cable impedance with the RF antenna and a biological tissue load impedance.

10. The device of claim 9, further comprising an interface unit coupled to the distal end portion of the cable, and an electrical conductor having a first end connected to the interface unit and a second end connected to the RF signal generator, the interface unit having an impedance matching electrical interface device connected to a distal end of the inner conductor and the distal end of the outer conductor of the elongate cable and to the first end of the electrical conductor.

11. The device of claim 10, wherein the interface device comprises a microstrip.

12. The device of claim 1, wherein the frequency comprises that of the microwave frequency range from approximately 300 MHz and up.

13. The device of claim 1, further comprising a shape control mechanism connected to the proximal end of the cable which controls the configuration of the distal end portion of the cable.

14. The device of claim 1, wherein a distal end of the hollow, axially extending lumen is closed.

15. The device of claim 1, wherein at least one of the first and second electrically conductive tubular members is formed of an electrically conductive wire mesh.

16. The device of claim 1, wherein at least one of the first and second electrically conductive tubular members is formed of an electrically conductive braided material.

17. The device of claim 1, wherein at least one of the first and second electrically conductive tubular members is formed of an electrically conductive thin-film material.

18. The device of claim 1, further comprising an outer layer of non-conductive material extending over the outer conductor.

19. The device of claim 1, further comprising an inner sleeve of non-conductive material extending inside the inner conductor, the hollow, axially extending lumen extending through the inner sleeve.

* * * * *